(12) United States Patent
Heckmann

(10) Patent No.: US 7,976,349 B2
(45) Date of Patent: Jul. 12, 2011

(54) COMMUNICATIONS PATCHING AND CONNECTOR SYSTEMS HAVING MULTI-STAGE NEAR-END ALIEN CROSSTALK COMPENSATION CIRCUITS

(75) Inventor: David Heckmann, Richardson, TX (US)

(73) Assignee: CommScope, Inc. of North Carolina, Hickory, NC (US)

( * ) Notice: Subject to any disclaimer, the term of this patent is extended or adjusted under 35 U.S.C. 154(b) by 0 days.

(21) Appl. No.: 12/632,855

(22) Filed: Dec. 8, 2009

(65) Prior Publication Data
US 2011/0136372 A1    Jun. 9, 2011

(51) Int. Cl.
*H01R 24/00* (2006.01)
(52) U.S. Cl. ...................................................... 439/676
(58) Field of Classification Search .................. 439/676, 439/941, 404, 620.21, 620.22
See application file for complete search history.

(56) References Cited

U.S. PATENT DOCUMENTS

| | | | |
|---|---|---|---|
| 5,459,643 A | 10/1995 | Siemon et al. | |
| 5,997,358 A | 12/1999 | Adriaenssens et al. | |
| 7,179,115 B2 | 2/2007 | Hashim | |
| 7,264,516 B2 | 9/2007 | Hashim et al. | |
| 7,427,218 B1 * | 9/2008 | Hashim et al. | 439/676 |
| 7,549,890 B2 | 6/2009 | Hashim | |
| 7,591,686 B2 * | 9/2009 | Ellis et al. | 439/676 |
| 7,682,203 B1 * | 3/2010 | Pharney et al. | 439/676 |
| 7,914,346 B2 * | 3/2011 | Pharney et al. | 439/676 |
| 2003/0186591 A1 | 10/2003 | Jensen et al. | |
| 2007/0111565 A1 | 5/2007 | Hashim | |
| 2008/0090468 A1 | 4/2008 | Reeves et al. | |
| 2010/0317230 A1 * | 12/2010 | Larsen et al. | 439/620.22 |

OTHER PUBLICATIONS

Combined Search and Examination Report under Sections 17 and 18(3) dated Dec. 20, 2010; Corresponding to UK Patent Application No. GB 1014330.3; 6 pages.
Leviton Category 6A jack having traces at edge of printed circuit board (see circles in pictures) that would be located next to conductive elements on an adjacently mounted jack (admitted prior art).

* cited by examiner

*Primary Examiner* — Chandrika Prasad
(74) *Attorney, Agent, or Firm* — Myers Bigel Sibley & Sajovec

(57) ABSTRACT

Communications patching devices include first and second connectors mounted immediately adjacent to each other. The first connector includes a first output terminal and a second output terminal that are connected to respective first and second conductive paths, and the second connector includes a third output terminal and a fourth output terminal that are connected to respective third and fourth conductive paths. The first and second conductive paths form a first differential pair of conductive paths and the first and second output terminals form a first differential pair of output terminals. The third and fourth conductive paths form a second differential pair of conductive paths, and the third and fourth output terminals form a second differential pair of output terminals. The output terminals are arranged such that a first signal coupling level from the first output terminal to the third output terminal in response to a communication signal that is transmitted through the first differential pair of output terminals exceeds a second signal coupling level from the first output terminal to the fourth output terminal in response to the communication signal. A first capacitor is provided between the first conductive path and the fourth conductive path and a second capacitor is provided between at least one of the first conductive path and the third conductive path or between the second conductive path and the fourth conductive path.

16 Claims, 8 Drawing Sheets

COMMUNICATIONS PATCHING AND CONNECTOR SYSTEMS HAVING MULTI-STAGE NEAR-END ALIEN CROSSTALK COMPENSATION CIRCUITS

FIELD OF THE INVENTION

The present invention relates generally to communications connectors and, more particularly, to communications connector systems that include alien crosstalk compensation circuits.

BACKGROUND

Dedicated communications systems that use communications cables and plug and jack connectors are commonly employed to enable computers, servers, printers, facsimile machines and other electronic devices to communicate with each other, through a private network, and with remote locations via a telecommunications service provider. Such communications system may be hard wired through, for example, the walls and/or ceilings of a building. Individual jacks such as RJ-45 style modular wall jacks are mounted in offices throughout the building. The communications cables provide a communications path from these jacks to network equipment (e.g., network servers, switches, etc.) that may be located in a computer room. Communications cables from external telecommunication service providers may also terminate within the computer room.

In the above-described communications systems, the communications cables that are connected to end devices are typically terminated into one or more communications patching systems that may simplify later connectivity changes. These communications patching systems typically include a plurality of "patch panels" that are mounted on one or more equipment racks. As is known to those of skill in the art, a "patch panel" refers to an inter-connection device that includes a plurality of connector ports (e.g., RJ-45 jacks) on a front side thereof. Each connector port is configured to receive a first communications cable that is terminated with a mating connector (e.g., an RJ-45 plug). Typically, a second communications cable is terminated into the reverse side of each connector port. With respect to a jack on an RJ-45 patch panels, the second communications cable is typically terminated into the reverse side of the patch panel by terminating the individual conductors of the cable into corresponding insulation displacement contacts or other wire connection terminals of the jack. Each connector port on the patch panel may provide communications paths between the first communications cable that is plugged into the front side of the connector port and the second communications cable that is terminated into the reverse side of the connector port.

FIG. 1 is a simplified example illustrating one way in which a communications patching system may be used to connect a computer (or other end device) 10 located in an office 4 of a building to network equipment 52, 54 located in a computer room 2 of the building. As shown in FIG. 1, the computer 10 is connected by a patch cord assembly 11 to a modular wall jack 20 that is mounted in a wall plate 16 in office 4. The patch cord assembly 11 comprises a communications cable 12 that contains a plurality of individual conductors and plugs 13, 14 that are attached to the respective ends of the cable 12. The plug 13 is inserted into a jack (not pictured in FIG. 1) that is provided in the computer 10, and the plug 14 inserts into a plug aperture 21 in the front side of the jack 20. The contacts or "blades" of plug 14 (which are exposed through the slots 15 on the top and front surfaces of plug 14) mate with respective contacts (not visible in FIG. 1) of the jack 20 when the plug 14 is inserted into the plug aperture 21. The blades of plug 13 similarly mate with respective contacts of the jack that is provided in the computer 10.

The jack 20 includes a back-end wire connection assembly 22 that receives and holds conductors from a communications cable 25. As shown in FIG. 1, each conductor of cable 25 is individually pressed into a respective one of a plurality of slots provided in the back-end connection assembly 22 to establish mechanical and electrical connection between each conductor of cable 25 and the jack 20. The communications cable 25 is routed from the back end of the wall jack 20 through, for example, the walls and/or ceiling of the building, to the computer room 2. As there may be hundreds or thousands of wall jacks 20 within an office building, a large number of cables 25 may be routed into the computer room 2.

A first equipment rack 30 is provided in the computer room 2. A plurality of patch panels 32 are mounted on the first equipment rack 30. Each patch panel 32 includes a plurality of connector ports 34 such as, for example, modular RJ-45 jacks. Each cable 25 that provides connectivity between the computer room 2 and the various offices 4 in the building is terminated onto the back end of one of the connector ports 34 of one of the patch panels 32. A second equipment rack 40 is also provided in the computer room 2. A plurality of patch panels 42 that include connector ports 44 are mounted on the second equipment rack 40. A first set of patch cords 46 (only two exemplary patch cords 46 are illustrated in FIG. 1) are used to interconnect the connector ports 34 on the patch panels 32 to respective ones of the connector ports 44 on the patch panels 42.

As is further shown in FIG. 1, network devices such as, for example, one or more network switches 52 and network routers and/or servers 54 are mounted on a third equipment rack 50. Each of the switches 52 may include a plurality of connector ports 53. A second set of patch cords 60 connect the connector ports 53 on the switches 52 to the back end of respective ones of the connector ports 44 on the patch panels 42. A third set of patch cords 64 may be used to interconnect other of the connector ports 53 on the switches 52 with connector ports 55 provided on the network routers/servers 54. In order to simplify FIG. 1, only a single patch cord 60 and a single patch cord 64 are shown. One or more external communications lines 66 may be connected to, for example, one or more of the network devices 54 (either directly or through a patch panel). The communications patching system of FIG. 1 thus may be used to connect each computer 10 and the like located throughout the building to the network routers and servers 54 and/or the external communications lines 66 through the network switches 52.

Typically, the information signals transmitted between networked devices (e.g., computer 10 and network server 54) are transmitted over a pair of conductors (hereinafter a "differential pair" or simply a "pair") rather than over a single conductor. The signals transmitted on each conductor of the differential pair have equal magnitudes, but opposite phases, and the information signal is embedded as the voltage difference between the signals carried on the two conductors of the pair. When signals are transmitted over a conductor in a cable, electrical noise from external sources such as lightning, electronic equipment, radio stations, etc. may be picked up by the conductor that degrade the quality of the information signal. When the signal is transmitted over a differential pair of conductors, each conductor in the differential pair often picks up approximately the same amount of noise from these external sources. Because approximately an equal amount of noise is added to the signals carried by both conductors of the differential pair, the information signal is typically not disturbed, as the information signal is extracted by taking the difference of the signals carried on the two conductors of the differential pair; thus, the noise signal is cancelled out by the subtraction process.

The cables and connectors in most high speed communications systems include eight conductors that are arranged as four differential pairs. The cascaded plugs, jacks and cabling segments shown in FIG. 1 that provide connectivity between two end devices (e.g., computer 10 and network server 54) is referred to herein as a "channel." Thus, in most high speed communications systems, a "channel" includes four differential pairs, as four differential pairs are typically provided in the cabling and connectors that are used to interconnect the two devices. Typically, the conductors in the communications cables and the contacting structures within communications connectors are located in close proximity to each other. As a result, energy from a signal that is transmitted over a first differential pair of the channel may capacitively and/or inductively couple to one or more of the other differential pairs. This capacitive and inductive coupling gives rise to another type of noise that is called "crosstalk."

More specifically, "crosstalk" refers to unwanted signal energy that is induced onto the conductors of a first "victim" differential pair from a signal that is transmitted over a second "disturbing" differential pair. The induced crosstalk may include both near-end crosstalk ("NEXT"), which is the crosstalk measured at an input location corresponding to a source at the same location (i.e., crosstalk whose induced voltage signal travels in an opposite direction to that of an originating, disturbing signal in a different path), and far-end crosstalk ("FEXT"), which is the crosstalk measured at the output location corresponding to a source at the input location (i.e., crosstalk whose signal travels in the same direction as the disturbing signal in the different path). Both types of crosstalk comprise an undesirable noise signal that interferes with the information signal on the victim differential pair.

Crosstalk that arises between two differential pairs that are part of the same channel is typically referred to as "internal" crosstalk. Because communications cables are often bundled together for routing through the walls, floors and/or ceilings of buildings and/or because communications connectors are often located in very close proximity to each other in, for example, patch panels and switches, crosstalk may also occur between one or more differential pairs of a first channel and one or more differential pairs of a second channel. Such crosstalk between differential pairs of different channels is typically referred to as "alien" crosstalk.

A variety of techniques may be used to reduce crosstalk in communications systems such as, for example, tightly twisting the paired conductors in a cable, whereby different pairs are twisted at different rates that are not harmonically related, so that each conductor of a first differential pair in the cable picks up approximately equal amounts of signal energy from the two conductors of each of the other differential pairs in the cable. Additionally, jacks and plugs have been developed that include crosstalk compensation circuits that introduce compensating crosstalk that is used to cancel much of the "offending" crosstalk that is unavoidably generated in many industry-standardized plug and jack designs.

SUMMARY

Pursuant to embodiments of the present invention, communications patching devices are provided that include first and second connectors mounted immediately adjacent to each other. The first connector includes a first output terminal and a second output terminal that are connected to respective first and second conductive paths, and the second connector includes a third output terminal and a fourth output terminal that are connected to respective third and fourth conductive paths. The first and second conductive paths form a first differential pair of conductive paths and the first and second output terminals form a first differential pair of output terminals. The third and fourth conductive paths form a second differential pair of conductive paths, and the third and fourth output terminals form a second differential pair of output terminals. The output terminals are arranged such that a first signal coupling level from the first output terminal to the third output terminal in response to a communication signal that is transmitted through the first differential pair of output terminals exceeds a second signal coupling level from the first output terminal to the fourth output terminal in response to the communication signal. A first capacitor is provided between the first conductive path and the fourth conductive path and a second capacitor is provided between at least one of the first conductive path and the third conductive path or between the second conductive path and the fourth conductive path.

In some embodiments, a first delay corresponding to a time it takes the first communication signal to travel from the first differential pair of output terminals to the first capacitor may be less than a second delay that corresponds to a time that it takes the first communication signal to travel from the first differential pair of output terminals to the second capacitor. The first, second, third and fourth output terminals may be mounted on a common printed circuit board. The output terminals may comprise insulation displacement contacts.

In some embodiments, the first and second capacitors comprise at least part of a multi-stage near-end alien crosstalk compensation circuit that is configured to compensate for near-end alien crosstalk between the first and second differential pairs of conductive paths. In such embodiments, the first capacitor may comprise at least part of a first stage of the multi-stage near-end alien crosstalk compensation circuit and the second capacitor may comprise at least part of a second stage of the multi-stage near-end alien crosstalk compensation circuit, and the polarity of the near-end alien crosstalk compensation introduced in the first stage maybe generally opposite the polarity of the near-end alien crosstalk compensation introduced in the second stage.

In some embodiments, the multi-stage near-end alien crosstalk compensation circuit may consist only of capacitive compensation elements. Moreover, the multi-stage near-end alien crosstalk compensation circuit may increase the far-end alien crosstalk between the first and second differential pairs of conductive paths.

The first electrode of the first capacitor may be directly connected to a first metal-plated aperture in the common printed circuit board that receives the first output terminal via a dead-end branch off of the first conductive path, and the second electrode of the first capacitor may be directly connected to a second metal-plated aperture in the common printed circuit board that receives the fourth output terminal via a dead-end branch off of the fourth conductive path. A third capacitor may also be provided between the second conductive path and the third conductive path.

Pursuant to further embodiments of the present invention, communications connector systems are provided that include a first communications connector that has a first insulation displacement contact ("IDC") and a second IDC, the first and second IDCs being connected to respective first and second conductive paths that comprise a first differential pair of conductive paths through the first connector. These systems further include a second communications connector that has a third IDC and a fourth IDC, the third and fourth IDCs being connected to respective third and fourth conductive paths that comprise a second differential pair of conductive paths through the second connector. The second connector is immediately adjacent to the first connector and arranged such that a first signal coupling level from the first IDC to the third IDC in response to a first communication signal that is transmitted through the first differential pair of output terminals exceeds a second signal coupling level from the first IDC to the fourth IDC in response to the first communication signal. The system further includes a multi-stage near-end alien crosstalk compensation circuit having at least a first stage and a second stage that is configured to compensate for near-end alien crosstalk between the first and second differential pairs of conductive paths the polarity of the near-end alien crosstalk introduced in the first stage is generally opposite the polarity of the near-end alien crosstalk introduced in the second stage and is also generally opposite the polarity of the near-end alien crosstalk introduced in the first through fourth IDCs.

In some embodiments, the first, second, third and fourth IDCs are mounted on a common printed circuit board. The multi-stage near-end alien crosstalk compensation circuit may consist only of capacitive compensation elements and/or may increase the far-end alien crosstalk between the first and second differential pairs of conductive paths. The first stage of the multi-stage near-end alien crosstalk compensation circuit may be located at substantially no delay from a base of the first IDC, and may comprise a first capacitor between the first conductive path and the fourth conductive path and a third capacitor between the second conductive path and the third conductive path.

Pursuant to further embodiments of the present invention, communications connector systems are provided that include a first communications connector that has a first output contact and a second output contact, the first and second output contacts being connected to respective first and second input contacts via respective first and second conductive paths through the first communications connector, the first and second output contacts, input contacts and conductive paths forming a first differential pair of communications paths through the first communications connector. These connector systems further include a second communications connector that has a third output contact and a fourth output contact, the third and fourth output contacts being connected to respective third and fourth input contacts via respective third and fourth conductive paths through the second communications connector, the third and fourth output contacts, input contacts and conductive paths forming a second differential pair of communications paths through the second communications connector. These connector systems also include a third communications connector that includes a fifth output contact and a sixth output contact, the fifth and sixth output contacts being connected to respective fifth and sixth input contacts via respective fifth and sixth conductive paths through the third communications connector, the fifth and sixth output contacts, input contacts and conductive paths forming a third differential pair of communications paths through the third communications connector. A first near-end alien crosstalk compensation circuit is provided that is configured to compensate for near-end alien crosstalk between the first differential pair of communications paths and the second differential pair of communications paths. A second near-end alien crosstalk compensation circuit is also provided that is configured to compensate for near-end alien crosstalk between the first differential pair of communications paths and the third differential pair of communications paths.

In some embodiments, the first near-end alien crosstalk compensation circuit comprises a multi-stage near-end alien crosstalk compensation circuit. The first through sixth output contacts may comprise insulation displacement contacts ("IDCs"), and the first near-end alien crosstalk compensation circuit may compensate at least primarily for near-end alien crosstalk between the IDCs of the first and second differential pairs of communications paths. The second near-end alien crosstalk compensation circuit may comprise a single-stage near-end alien crosstalk compensation circuit. The first through sixth input contacts may comprise contact wires, and the second near-end alien crosstalk compensation circuit may compensate at least primarily for near-end alien crosstalk between the contact wires of the first and third differential pairs of communications paths.

DETAILED DESCRIPTION

Figure 1:
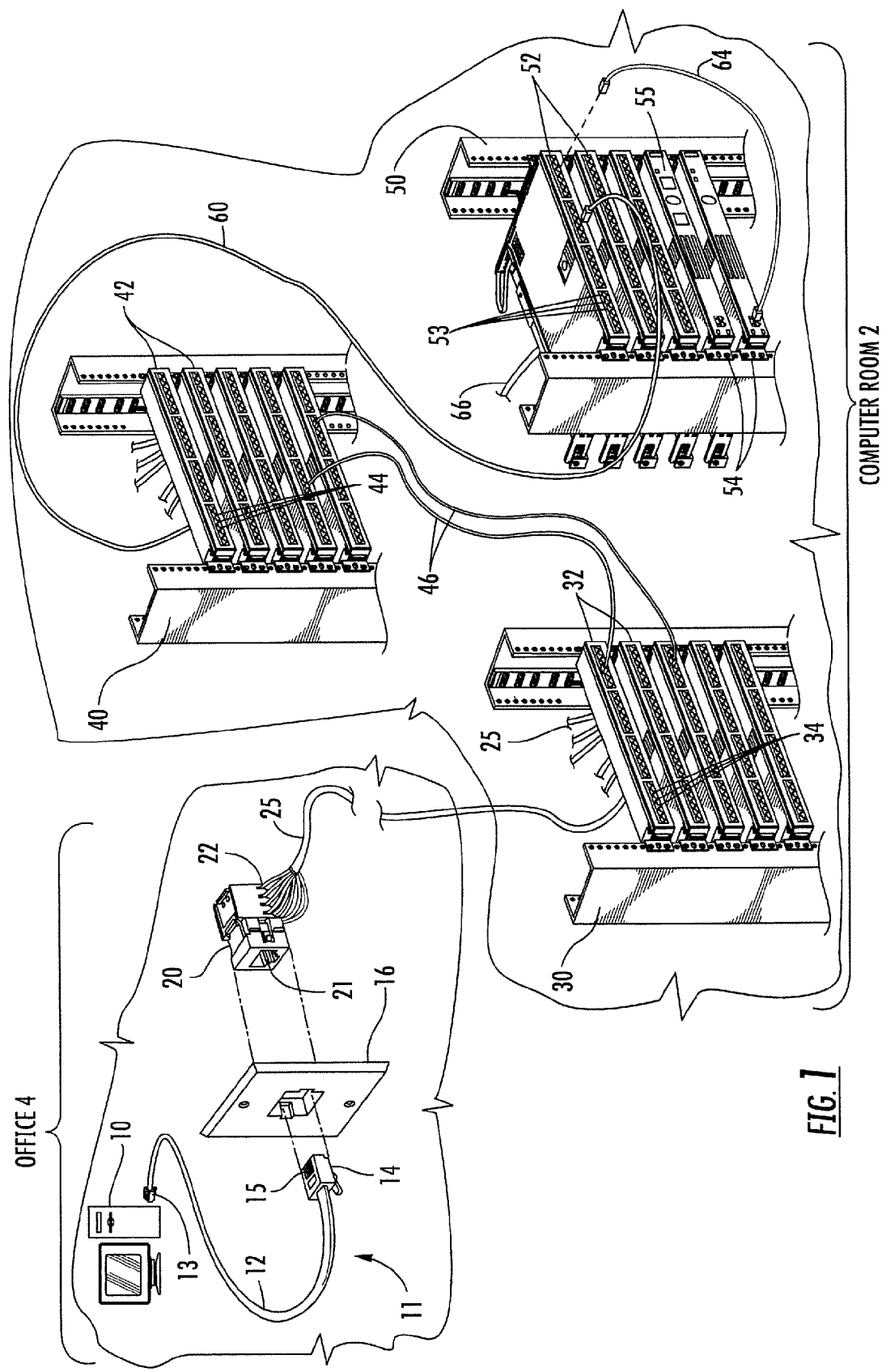
FIG. 1 is a schematic drawing that illustrates the use of plug-jack connectors to connect a computer to network equipment.

The present invention will be described more particularly hereinafter with reference to the accompanying drawings. The invention is not limited to the illustrated embodiments;

rather, these embodiments are intended to fully disclose the invention to those skilled in this art. In the drawings, like numbers refer to like elements throughout. The dimensions of some components may be exaggerated for clarity.

Spatially relative terms, such as "under", "below", "lower", "over", "upper", "top", "bottom" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity. As used herein the expression "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes" and/or "including" when used in this specification, specify the presence of stated features, operations, elements, and/or components, but do not preclude the presence or addition of one or more other features, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Herein, the terms "attached", "connected", "interconnected", "contacting", "mounted" and the like encompass both direct or indirect attachment, connection or contact between elements, unless stated otherwise.

Herein, the term "conductive trace" refers to a conductive segment that extends from a first point to a second point on a printed circuit board. Typically, a conductive trace comprises an elongated strip of copper or other metal that extends on the printed circuit board from the first point to the second point. Herein, the term "printed circuit board" is used broadly to cover any wiring board.

Herein, the term "signal current carrying path" is used to refer to a current carrying path on which an information signal will travel on its way from an input to a respective output of a communications connector (e.g., a plug, a jack, a mated-plug jack connection, etc.). Signal current carrying paths may be formed by cascading one or more conductive traces on a printed circuit board, metal-filled apertures that physically and electrically connect conductive traces on different layers of a printed circuit board, portions of contact wires or plug blades, conductive pads, and/or various other electrically conductive components over which an information signal may be transmitted through the communications connector from the input to the respective output. Branches that extend from a signal current carrying path and then dead end, such as, for example, a branch from the signal current carrying path that connects to an electrode of a plate capacitor or an interdigitated finger capacitor, are not considered part of the signal current carrying path, even though these branches are electrically connected to the signal current carrying path. While a small amount of current (e.g., 1% of the current incident at an input of the connector at 100 MHz, or perhaps 5% of the current incident at the input of the connector at 500 MHz) will flow into such dead end branches, the current that flows into these dead end branches generally does not flow to the output of the connector that corresponds to the input of the connector that receives the input information signal. Herein, the current that flows into such dead end branches is referred to as a "coupling current," whereas the current that flows along a signal current carrying path is referred to herein as a "signal current."

Pursuant to embodiments of the present invention, communications connector systems are provided that include near-end alien crosstalk compensation circuits. These communications connector systems may comprise patch panels, multi-jack wall outlets, network switches or any other communications connector systems that includes at least two closely spaced communications connectors (e.g., jacks). The connectors in these systems may use multi-stage crosstalk compensation techniques to reduce near-end alien crosstalk between differential pairs of adjacent connectors to very low levels. In some embodiments, the communications connector system may comprise a patch panel, and the multi-stage near-end alien crosstalk compensation system may comprise a plurality of capacitors that are used to compensate for near-end alien crosstalk between adjacent jacks in the patch panel.

As noted above, crosstalk (both internal and alien) arises when a first conductor of a first differential pair inductively and/or capacitively couples more heavily with a first of the two conductors of a second differential pair than it does with the second conductor of the first differential pair. Such crosstalk is often referred to as "offending" crosstalk because it represents an undesired coupling that typically arises due to industry-standardized plug and jack interfaces and/or from a desire to closely pack communications cables and connectors together to reduce or minimize the space requirements of the network communications system. In order to compensate for such offending crosstalk, jacks and plugs have been purposefully designed so that the second conductor of the first differential pair would capacitively and/or inductively couple with the first of the two conductors of the second differential pair later in the jack to provide a "compensating" crosstalk signal. As the first and second conductors of the differential pair carry equal magnitude, but opposite phase signals, so long as the magnitude of the "compensating" crosstalk signal that is induced in such a fashion is equal to the magnitude of the "offending" crosstalk signal, then the compensating crosstalk signal that is introduced later in the jack may substantially cancel out the offending crosstalk signal. This crosstalk compensation technique is often referred to as single-stage crosstalk compensation, and is well known in the art. U.S. Pat. No. 5,186,647 to Denkmann et al. and U.S. Pat. No. 5,326,284 to Bohbat et al. illustrate jacks that include exemplary single-stage crosstalk compensation circuits.

Figure 2:
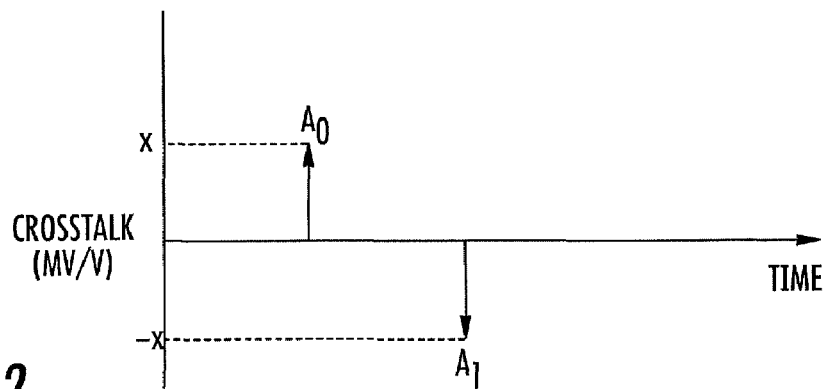
FIG. 2 is a schematic graph of crosstalk versus time that illustrates the offending and compensating crosstalk (depicted as lumped approximations) in a plug-jack connector employing a single-stage crosstalk compensation circuit.

FIG. 2 is a schematic graph of coupling between two differential pairs as a function of time that illustrates how a conventional single-stage crosstalk compensation circuit works. As shown in FIG. 2, at a first location in the plug-jack connector (which may be a discrete point or which may be distributed over some distance), the first conductor of a first differential pair of conductive paths through the connector couples (inductively and/or capacitively) more heavily with a first of the two conductors of a second differential pair of conductive paths through the connector than does the second conductor of the first differential pair. As a result, the coupling from the second conductor of the first differential pair only partially cancels out the coupling from the first conductor of the first differential pair, and the remaining coupling from the first conductor of the first differential pair onto the first conductor of the second differential pair appears as an "offending" crosstalk signal that interferes with any communications signal carried by the second differential pair. This offending crosstalk signal is represented by vector $A_0$ in FIG. 2, where the length of the vector represents the magnitude of the crosstalk and the direction of the vector (up or down) represents the polarity (positive or negative) of the crosstalk. For purposes of illustration, it is assumed in FIG. 2 that vector $A_0$ has a positive polarity. As noted above, the unequal coupling that generates the offending crosstalk may occur for some distance along the conductive paths, and hence the offending crosstalk may be distributed to some extent over the time axis. However, for ease of description, this distributed offending crosstalk is represented as a single crosstalk vector $A_0$ in FIG. 2 that has a magnitude equal to the sum of the distributed crosstalk that is located at the weighted midpoint of the differential coupling region (referred to herein as a "lumped approximation").

In order to implement a single-stage crosstalk compensation scheme, a crosstalk compensation circuit is provided at a second location in the connector. In this crosstalk compensation circuit, the second conductor of the first differential pair capacitively and/or inductively couples more heavily with the first of the two conductors of the second differential pair than does the first conductor of the first differential pair. (Alternatively and/or additionally, the crosstalk compensation circuit may couple the first conductor of the first differential pair with the second conductor of the second differential pair.) As a result of this unequal coupling, a compensating crosstalk signal is generated that is represented by the vector $A_1$ in FIG. 2. Moreover, since the signal carried by, for example, the second conductor of the first differential pair is 180 degrees out-of-phase with the signal carried by the first conductor of the first differential pair, the polarity of the compensating crosstalk signal is opposite the polarity of the offending crosstalk signal, and hence vector $A_1$ has a negative value in FIG. 2. The crosstalk compensation circuit is designed so that the magnitude of the compensating crosstalk signal $A_1$ is equal to the magnitude of the offending crosstalk signal $A_0$. Since the two crosstalk signals $A_0$ and $A_1$ are equal in magnitude but opposite in phase, the compensating crosstalk signal (represented by vector $A_1$ in FIG. 2) may substantially cancel the offending crosstalk signal (represented by vector $A_0$ in FIG. 2).

The signals carried on the conductors of the cables and connectors are alternating current signals, and hence the phase of the signal changes with time. Typically, the distance between the location where the offending crosstalk is generated and the location of the compensating crosstalk circuit is quite small, and hence the time difference (delay) between the generation of the offending crosstalk and the generation of the compensating crosstalk is also small. Thus, for lower frequency signals (e.g., signals having a frequency less than 100 MHz), the amount that the phase of a signal will change when travelling from the location of vector $A_0$ to the location of vector $A_1$ in FIG. 2 is small, and thus vector $A_t$ will be almost 180 degrees out of phase with vector $A_0$. Consequently, for lower frequency signals, a single-stage crosstalk compensation circuit can almost exactly cancel out an offending crosstalk signal.

Figure 3A:
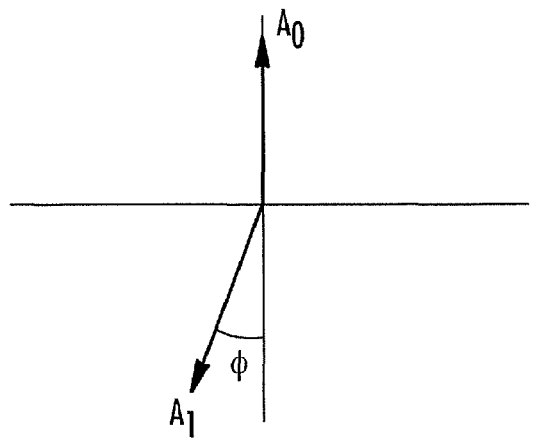
FIG. 3A is a vector diagram that illustrates how delay can impact the effectiveness of a single-stage crosstalk compensation circuit.
Figure 3B:
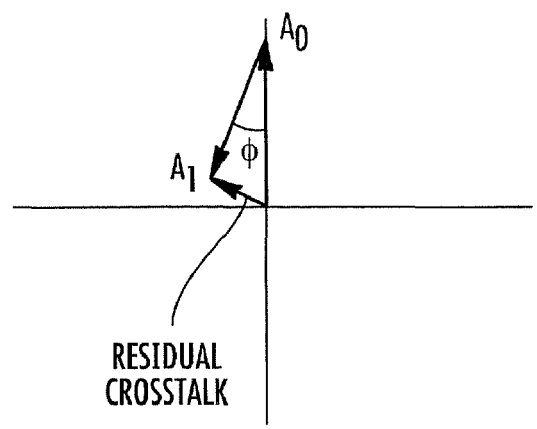
FIG. 3B is a vector summation diagram that illustrates how the vectors of FIG. 3A will not sum to zero for higher frequency signals due to the phase shift between vectors $A_0$ and $A_1$.

However, for higher frequency signals, the amount that the phase of a signal will change when traveling from the location of vector $A_0$ to the location of vector $A_1$ in FIG. 2 can become significant. FIG. 3A is a vector diagram (on a polar coordinate system) that illustrates how the phase of compensating crosstalk vector $A_1$ will change by an angle $\phi$ due to the time delay between vectors $A_0$ and $A_1$. The higher the frequency of the signal carried over the first differential pair is, the greater the angle $\phi$. As shown in FIG. 3A, because of this phase change vector $A_1$ is offset from vector $A_0$ by an angle of $180°-\phi$, where the value of $\phi$ increases with increasing frequency. For very small values of $\phi$, vector $A_1$ will almost perfectly cancel vector $A_0$, but the degree of cancellation degrades significantly as the frequency (and hence the value of $\phi$) increases. This can be seen graphically in FIG. 3B, which illustrates how the addition of vectors $A_0$ and $A_1$ still leaves a residual crosstalk vector due to the phase change. FIG. 3B also makes clear that the degree of cancellation decreases as $\phi$ gets larger. Thus, due to the increased phase change at higher frequencies, the above-described single-stage crosstalk compensation scheme cannot fully compensate for the offending crosstalk.

U.S. Pat. No. 5,997,358 to Adriaenssens et al. (hereinafter "the '358 patent") describes multi-stage crosstalk compensation schemes for plug-jack connectors that can be used to provide significantly improved crosstalk cancellation, particularly at higher frequencies. The entire contents of the '358 patent are hereby incorporated herein by reference as if set forth fully herein. Pursuant to the teachings of the '358 patent, two or more stages of compensating crosstalk are added, usually in the jack, that together reduce or substantially cancel the offending crosstalk at the frequencies of interest.

As discussed in the '358 patent, the magnitude and phase of the compensating crosstalk signal(s) induced by each stage are selected so that, when combined with the compensating crosstalk signals from the other stages, they provide a composite compensating crosstalk signal that substantially cancels the offending crosstalk signal over a frequency range of interest. In embodiments of these multi-stage compensation schemes, the first compensating crosstalk stage (which can include multiple sub-stages) has a polarity that is opposite the polarity of the offending crosstalk, while the second compensating crosstalk stage has a polarity that is the same as the polarity of the offending crosstalk.

Figure 4A:
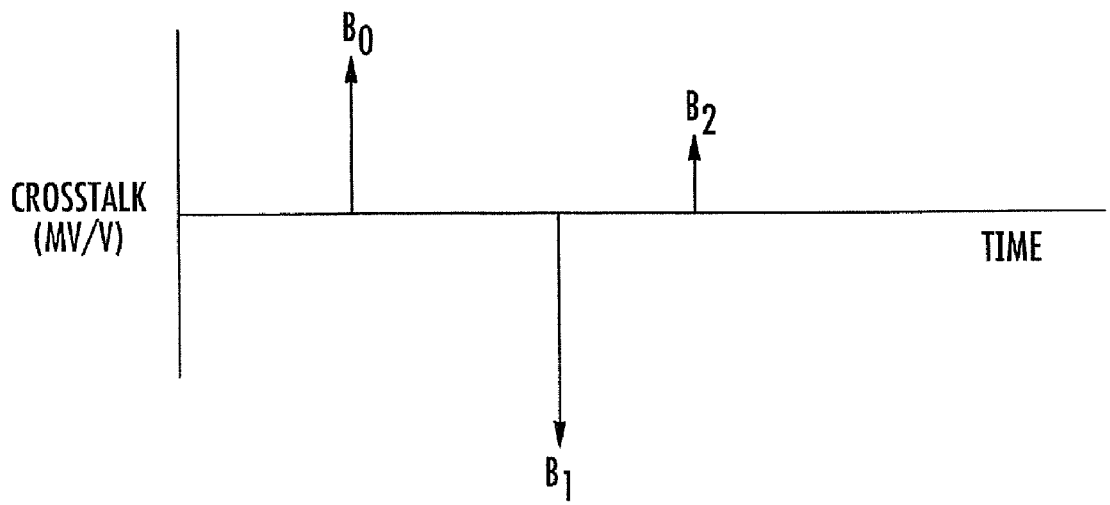
FIG. 4A is a schematic graph of crosstalk versus time that illustrates the offending and compensating crosstalk (depicted as lumped approximations) in a plug-jack connector that implements multi-stage crosstalk compensation.

FIG. 4A is a schematic graph of crosstalk versus time that illustrates the location of the offending and compensating crosstalk (depicted as lumped approximations) for an exemplary two-stage crosstalk compensation scheme. As shown in FIG. 4A, the offending crosstalk signal can be represented by the vector $B_0$ which has a magnitude equal to the sum of the distributed offending crosstalk and which is located at the weighted midpoint of the coupling region where the offending crosstalk is induced. As is further shown in FIG. 4A, the compensating crosstalk circuit induces a second crosstalk signal which is represented by the vector $B_1$. The crosstalk compensation circuit is typically located at a different location in the connector than the location where the offending crosstalk is generated, and hence the first stage compensating crosstalk vector $B_1$ is at a different location on the horizontal time axis than is the offending crosstalk vector $B_0$, since it takes some amount of time for a signal to travel from the offending crosstalk region to the first stage crosstalk compensation circuit. As is also shown in FIG. 4A, the compensating crosstalk vector $B_1$ has a polarity that is opposite to the polarity of the offending crosstalk vector $B_0$, similar to the compensating crosstalk vector $A_1$ in FIGS. 2 and 3A-3B. However, unlike vector $A_1$, the magnitude of the compensating crosstalk vector $B_1$ is larger than the magnitude of the offending crosstalk vector $B_0$. Finally, the compensating crosstalk circuit generates a second compensating crosstalk vector $B_2$ that is located even farther to the right on the time axis. The compensating crosstalk vector $B_2$ has a polarity that is opposite the polarity of crosstalk vector $B_1$, and hence has a polarity that is the same as the polarity of the offending crosstalk vector $B_0$. The magnitude of compensating crosstalk vector $B_2$ is typically smaller than the magnitude of both vectors $B_0$ and $B_1$. It will be appreciated that communications connectors typically are used to transmit signals in both the forward and reverse directions. Thus, were the direction of signal travel reversed, the signal travelling through the connector corresponding to FIG. 4A would first come to the second stage crosstalk compensation circuit (vector $B_2$), then to the first stage crosstalk compensation circuit (vector $B_1$), and finally to the offending crosstalk region (vector $B_0$).

Figure 4B:
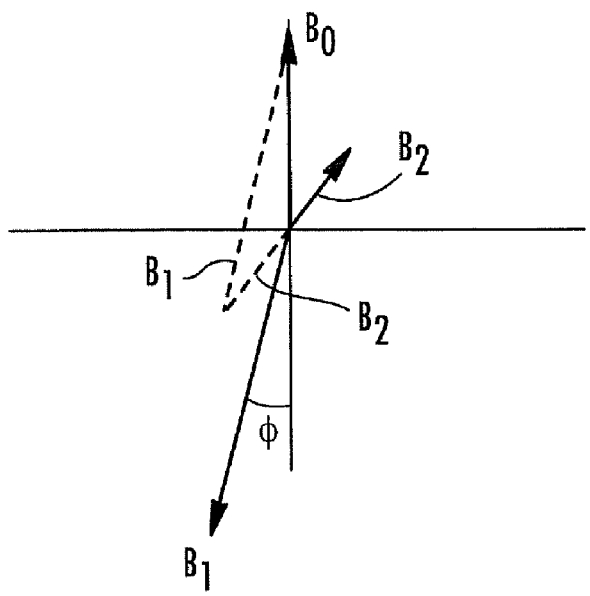
FIG. 4B is a vector summation diagram that illustrates how the multi-stage compensation crosstalk vectors $B_1$ and $B_2$ of FIG. 4A can cancel the offending crosstalk $B_0$ at a selected frequency.

FIG. 4B is a vector summation diagram that illustrates how the multi-stage compensation crosstalk vectors $B_1$ and $B_2$ of FIG. 4A can cancel the offending crosstalk vector $B_0$ at a selected frequency. FIG. 4B plots the crosstalk vectors from FIG. 4A on a vector diagram in a polar coordinate system that visually illustrates the magnitude and phase of each crosstalk vector. In FIG. 4B, the dotted line versions of vectors $B_1$ and $B_2$ are provided to show how the three vectors $B_0$, $B_1$ and $B_2$ may be designed to sum to approximately zero at a selected frequency. In particular, as shown in FIG. 4B, the first compensating crosstalk stage ($B_1$) overcompensates the offending crosstalk (and hence the sum of vectors $B_0$ and $B_1$, as shown by the dotted line version of vector $B_1$ extending from the end of vector $B_0$, is below the x-axis in FIG. 4B). The second compensating crosstalk stage ($B_2$) is then used to bring the sum of the crosstalk back to the origin of the graph (indicating substantially complete cancellation at the selected frequency). The multi-stage (i.e., two or more) compensation schemes disclosed in the '358 patent thus can be more efficient at reducing the NEXT and FEXT than schemes in which the compensation is added at a single stage.

Figure 5:
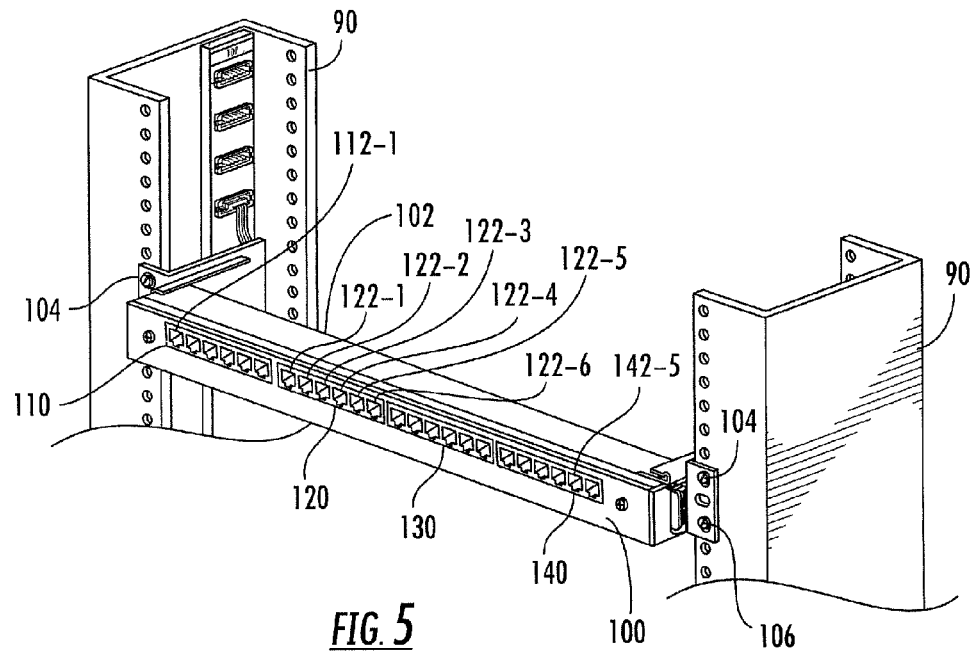
FIG. 5 is a perspective view of a patch panel according to certain embodiments of the present invention.
Figure 6:
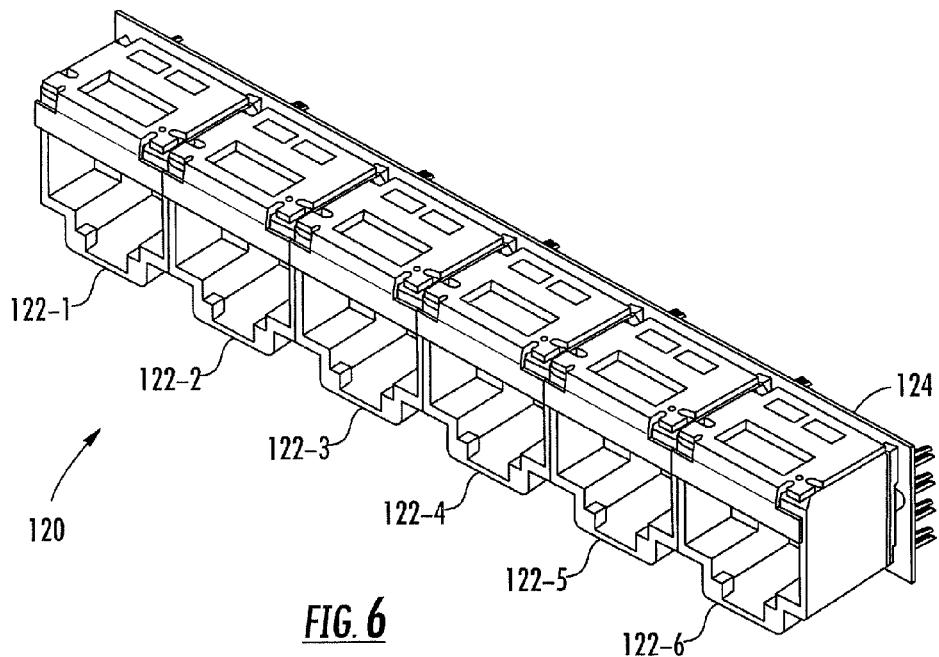
FIG. 6 is a perspective view of a communications insert of the patch panel of FIG. 5.
Figure 7:
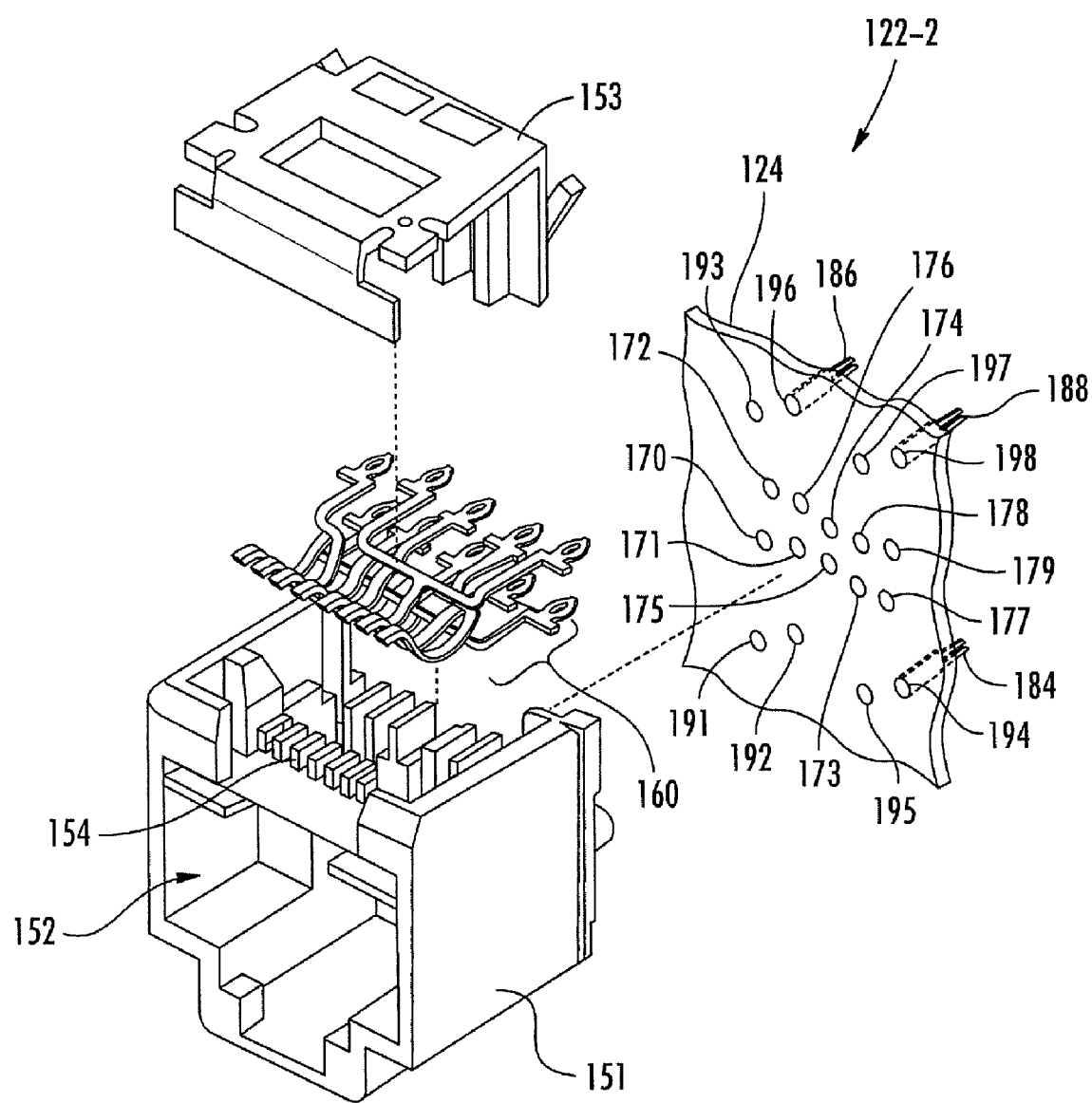
FIG. 7 is an enlarged, exploded perspective view of one of the jacks of the patch panel of FIG. 5.
Figure 8:
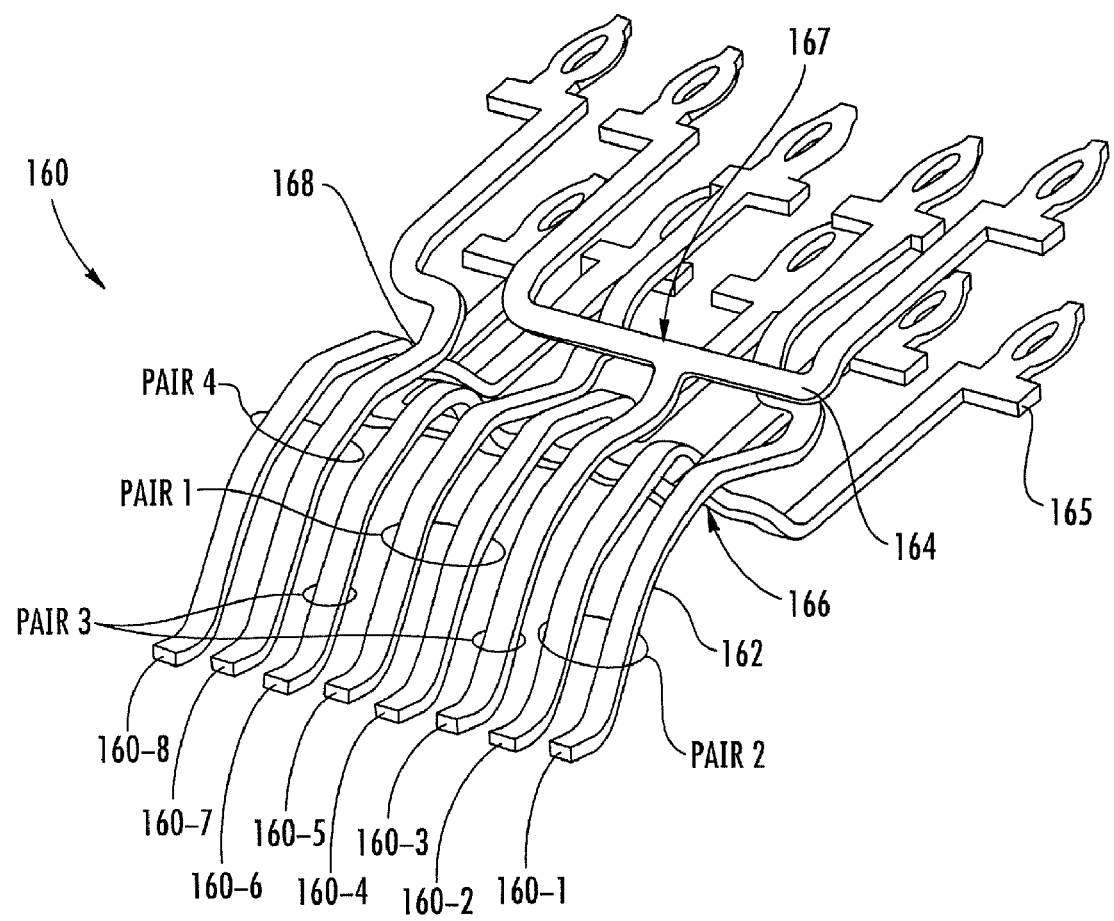
FIG. 8 is an enlarged view of the contact wires of the jack of FIG. 7.
Figure 9:
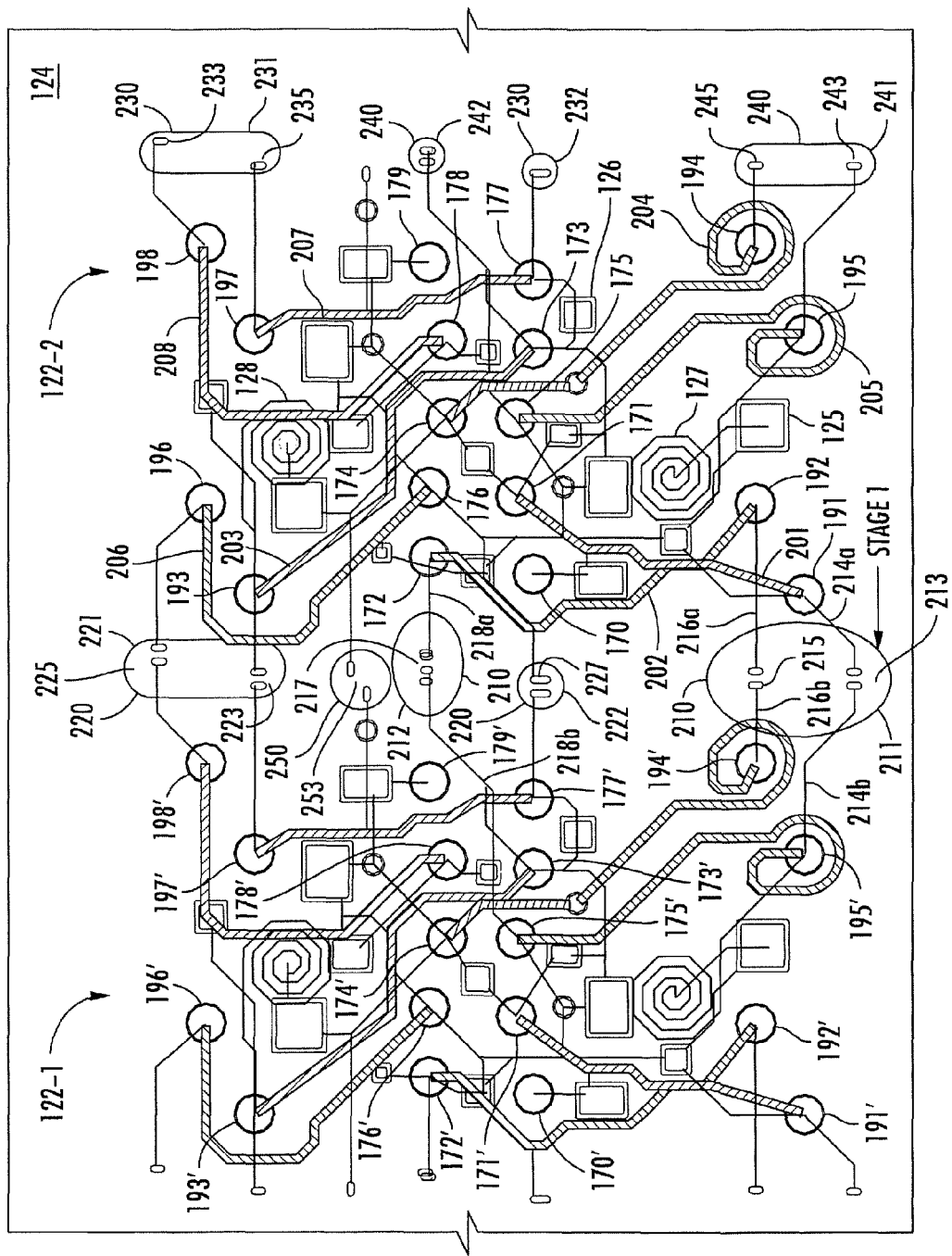
FIG. 9 is a plan view of the printed circuit board of the communications insert of FIG. 6.

FIGS. 5-9 illustrate a communications connector system according to certain embodiments of the present invention that includes multi-stage near-end alien crosstalk compensation circuits. In particular, FIG. 5 is a perspective view of a patch panel 100 according to certain embodiments of the present invention. FIG. 6 is a perspective view of a communications insert 120 of the patch panel 100 of FIG. 5. FIG. 7 is an enlarged, exploded perspective view of one of the jacks 122-2 included in the communications insert 120 of the patch panel 100. FIG. 8 is an enlarged view of the contact wires of the jack 122-2 of FIG. 7. Finally, FIG. 9 is a plan view of a printed circuit board 124 of the communications insert 120 of FIG. 6.

As shown in FIG. 5, the patch panel 100 may be mounted, for example, on vertical frame members of a communications equipment rack 90. The patch panel 100 includes a mounting frame 102, and four communications inserts 110, 120, 130, 140. The mounting frame may include apertures 104 at each end thereof which receive screws or bolts 106 that may be used to mount the patch panel 100 on the vertical frame members of communications equipment rack 90. Each communications insert 110, 120, 130, 140 includes six communications jacks 112-1 through 112-6; 122-1 through 122-6; 132-1 through 132-6; 142-1 through, 142-6, respectively. Jacks 112-1 through 112-6 are mounted on a first common printed circuit board 114, jacks 122-1 through 122-6 are mounted on a second common printed circuit board 124, jacks 132-1 through 132-6 are mounted on a third common printed circuit board 134, and jacks 142-1 through 142-6 are mounted on a fourth common printed circuit board 144. While the first through fourth common printed circuit boards 114, 124, 134, 144 are not visible in FIG. 5, FIG. 9 illustrates the design of printed circuit board 124 in detail. Printed circuit boards 114, 134 and 144 may be identical to printed circuit board 124.

FIG. 6 is a perspective view of communications insert 120. The communications inserts 110, 130, 140 may each be identical to the communications insert 120, and hence will not be described further herein. As shown in FIG. 6, the communications insert 120 includes six communications jacks 122-1 through 122-6. Each of the jacks 122-1 through 122-6 is mounted on a common printed circuit board 124. This common printed circuit board 124 comprises part of each jack 122-1 through 122-6. The jacks 122-1 through 122-6 are mounted in close proximity to each other. As a result, alien crosstalk can arise between adjacent of the jacks 122-1 through 122-6, between jack 122-1 and jack 112-6 of communications insert 110, and between jack 122-6 and jack 132-1 of communications insert 130 (see FIG. 5).

FIG. 7 is an exploded perspective view of jack 122-2 of communications insert 120. As shown in FIG. 7, the jack 122-2 includes a jack frame 151 that includes a plug aperture 152 for receiving a mating plug, a cover 153, a plurality of contact wires which are broadly designated as 160 (designated individually as 160-1 through 160-8 in FIG. 8), a portion of the printed circuit board 124, a plurality of insulation displacement contacts ("IDCs") 181-188, and an IDC cover (not shown in the figures).

The jack frame 151 has an opening into a plug aperture 152 on a front side thereof. The plug aperture 152 comprises a cavity that is sized and configured to receive a mating communications plug. The cover 153 may generally have an "L" shape. The cover 153 extends across the top of the jack frame 151, and part of the cover 153 may complete a back wall of the jack frame 151. The jack frame 151, the cover 153 and the IDC cover (not shown in the figures) together comprise a housing that defines the plug aperture 152 and protects other of the components of the communications jack 122-2. The jack frame 151, the cover 153 and the IDC cover may be made of a suitable insulative plastic material such as polycarbonate, ABS, and/or blends thereof that meets all applicable standards with respect to, for example, electrical breakdown resistance and flammability. The jack frame 151, the cover 153 and the IDC cover may be conventionally formed and hence will not be described in further detail herein. Those skilled in this art will recognize that a wide variety of other configurations of housings may also be employed in embodiments of the present invention, and that the housing may comprise more or less pieces than the exemplary housing illustrated in FIG. 7.

The contact wires 160 each comprise a conductive element that is used to make physical and electrical contact with a respective contact on a mating communications plug. The contact wires 160 may comprise spring contact wires (also referred to as "jackwire contacts) that are formed of resilient metals such as spring-tempered phosphor bronze, beryllium copper, or the like. A typical cross section of each contact wire 160 is 0.017 inches wide by 0.010 inches thick. As shown in FIG. 7, the contact wires 160 are mounted on the printed circuit board 124 in cantilever fashion by inserting each contact wire 160 in a respective one of a plurality of contact wire apertures 170-179 in the printed circuit board 124 so that the contact wires 160 are cantilevered from the rear of the jack 122-2 to extend into the plug aperture 152.

FIG. 8 is an enlarged perspective view of the contact wires 160-1 through 160-8 that more clearly illustrates the paths traversed by each contact wire. Note that in FIG. 8 the contact wires 160 have been rotated 180 degrees from their orientation in FIG. 7.

As shown in FIG. 8, the contact wires 160 (which are individually labeled as contact wires 160-1 through 160-8) are arranged in differential pairs as defined by the TIA/EIA-568-B.2-1 standard approved Jun. 20, 2002 by the Telecommunications Industry Association and the reference documents cited therein. In particular, contact wires 160-4, 160-5 form a first differential pair (pair 1) of contact wires that may be used to carry a first differential signal, contact wires 160-1, 160-2 form a second differential pair (pair 2) of contact wires that may be used to carry a second differential signal, contact wires 160-3, 160-6 form a third differential pair (pair 3) of contact wires that may be used to carry a third differential signal, and contact wires 160-7, 160-8 form a fourth differential pair (pair 4) of contact wires that may be used to carry a fourth differential signal. Thus, the communication jack 122-2 may carry up to four differential signals at a time that are carried on the four differential pairs of contact wires described above to respective ones of four differential pairs of conductive paths on the printed circuit board 124, to respective pairs of the IDCs 181-188, which are also arranged as differential pairs. As shown in FIG. 8, contact wires 160-4, 160-5 are in the center positions in the contact wire array, contact wires 160-1, 160-2 are adjacent to each other and occupy the rightmost two positions (from the vantage point of FIG. 8) in the sequence, and contact'wires 160-7, 160-8 are adjacent to each other and occupy the leftmost two positions (from the vantage point of FIG. 8) in the sequence. Contact wires 160-3, 160-6 are positioned so that, in the plug contact regions of the contact wires, these contact wires sandwich contact wires 160-4 and 160-5.

As shown in FIGS. 7-8, each of the contact wires 160 has a deflectable portion 161 that extends into the plug aperture 152 and a fixed termination end 165 that is mounted in the common printed circuit board 124. The deflectable portion 161 of each contact wire 160 refers to the portion of the contact wire 160 that moves when a mating plug is received within the plug aperture 152. The deflectable portion 161 of each contact wire 160 includes a plug contact region 162 which refers to the portion of the contact wire that is configured to make physical contact with a respective one of the contacts (e.g., plug blades) on a mating plug. The plug contact regions 162 of all eight contact wires may be generally aligned in a side-by-side relationship as shown in FIGS. 7-8. The deflectable portion 161 of contact wires 160-3 and 160-6 each further include a crossover section 164 where the contact wire crosses over and/or under one or more of the other contact wires when the contact wires 160 are viewed from above (i.e., when looking down at the jack 122-2 through the cover 153). The free end of each contact wire 160 (i.e., the forward end of the deflectable portion 161 of each contact wire 160) may extend into a respective one of the individual slots in the comb structure 154 on the jack frame 151 (see FIG. 7).

The fixed termination end 165 of each of the contact wires 160 comprises an "eye-of-the-needle" termination (or some other press-fit termination that may be inserted into a metal-plated aperture on the printed circuit board 124 without the need for a soldered connection). The rear wall of the jack frame 151 includes a plurality of vertical slots. The cover 153 includes mating projections (not visible in FIG. 7) that fill the vertical slots in the rear wall. A portion of each contact wire 160 passes through one of the vertical slots in the rear wall, and when the cover 153 is placed on the jack frame 151 each projection thereon captures a respective one of the contact wires 160 and locks it into place. The press-fit termination of each contact wire 160 passes through an opening between the vertical slot in the rear wall and the corresponding projection on the cover 153 so as to extend outside the rear of jack frame 151 for mating with the printed circuit board 124.

As can best be seen in FIG. 8, the contact wires 160-1, 160-2 of pair 2, the contact wires 160-3, 160-6 of pair 3, and the contact wires 160-7, 160-8 of pair 4 each include a respective "crossover." These crossovers are labeled 166, 167, 168 in FIG. 8. Herein, the term "crossover" is used to refer to a location in which the contact wires of a differential pair of contact wires cross each other without making electrical contact when the contact wires are viewed from above (i.e., through the cover 153). Crossovers are included to provide compensatory crosstalk between contact wires. Each of the crossovers 166, 167, 168 may be located in the deflectable portions 161 of the contact wires 160, and may be located close to the plug contact regions 162 in order to limit the degree of offending crosstalk and to generate compensating crosstalk as close as possible to the plug contact region 162. In the illustrated embodiment, the crossovers 166, 168 are implemented via complementary localized bends in the crossing contact wires, with one wire being bent upwardly and the other wire being bent downwardly. The crossover 167 is implemented by including a second termination end 169 on each of contact wires 160-3 and 160-6 (in addition to the standard fixed termination end 165) along with a crossover section 164 that connects the standard fixed termination end 165 and the second termination end 169.

FIG. 9 is a plan view of the portion of the printed circuit board 124 that jack 122-2 and adjacent jack 122-1 are mounted on. As is readily apparent from FIG. 9, the portion of the printed circuit board that corresponds to each of the individual jacks (e.g., jacks 122-1 and 122-2) may be identical. Consequently, only the right-hand side of FIG. 9, which corresponds to jack 122-2, will be described herein, and it will be appreciated that the corresponding elements of the portion of the printed circuit board 124 that is part of jack 122-1 may operate in the same fashion as the portion of the printed circuit board 124 that is part of jack 122-2. It will also be appreciated that the printed circuit board 124 is three times as large as shown, and includes an additional portion that extends to the right in FIG. 9 that includes conductive traces for jacks 122-3 through 122-6 (with the conductive traces for jack 122-3 being immediately to the right of the conductive traces for jack 122-2). This additional portion of the printed circuit board 124 may be identical to the portion of printed circuit board 122 that is pictured in FIG. 9 (repeated twice), and hence this additional portion of the printed circuit board 124 is neither shown in FIG. 9 or described further herein.

The printed circuit board 124 is a four-layer printed circuit board that includes a plurality of conductive traces and/or other conductive elements such as plate capacitors, conductive trace capacitors and spirals on the various layers thereof. In order to differentiate between layers, different cross-hatching schemes are used in FIG. 9 to show which traces are resident on each of the four layers of the printed circuit board 124 (where two traces overlap, only the top trace is shown in FIG. 9). The plates of the plate capacitors are not cross-hatched. However, it will be understood that, for each plate capacitor, a plate is provided on the same layers as the traces shown in FIG. 9 that electrically connect to the capacitors.

As shown in FIG. 9, the portion of the printed circuit board 124 corresponding to jack 122-2 includes a plurality of metal-plated apertures 171-178 that receive the termination ends 165 of the contact wires 160-1 through 160-8 and two additional metal-plated apertures 170, 179 that receive the two second termination ends 169 of contact wires 160-3 and 160-6. The printed circuit board 124 further includes a plurality of metal-plated apertures 191-198 that each receive the eye-of-the needle terminations of a respective one of the IDCs 181-188. The printed circuit board 124 also includes a plurality of conductive paths 201-208 that connect each of the metal-plated apertures 171-178 to a respective one of the metal-plated apertures 191-198. Each conductive path 201-208 thus provides an electrical path that may be used to carry a signal that is incident on one of the contact wires 160-1 through 160-8 to a respective one of the IDCs 181-188 (or vice versa). As shown in FIG. 9, some of the conductive paths 201-208 are implemented as a single conductive trace on a single layer of the printed circuit board 124 that directly connects one of the metal-plated apertures that 171-178 to a respective one of the metal-plated apertures 191-198, while other of the conductive path may include multiple conductive traces that reside on multiple layers of the printed circuit board 124 that are connected through metal filled apertures or other layer transferring techniques known to those skilled in the art.

Conductive paths 204 and 205 are connected to contact wires 160-4, 160-5, respectively, and form a first differential pair (pair 1) of conductive paths, conductive paths 201 and 202 are connected to contact wires 160-1, 160-2, respectively, and form a second differential pair (pair 2) of conductive paths, conductive paths 203 and 206 are connected to contact wires 160-3, 160-6, respectively, and form a third differential pair (pair 3) of conductive paths, and conductive paths 207 and 208 are connected to contact wires 160-7, 160-8, respectively, and form a fourth differential pair (pair 4) of conductive paths. It will be appreciated that the contact wires and IDCs that are connected to each differential pair of conductive paths may be considered to be part of the differential pair of conductive paths, depending upon whether reference is being made to a conductive path through the printed circuit board 124 (which would not include the contact wires or IDCs) or a conductive path through the jack 122-2 (which would include the contact wires and IDCs).

The portion of the printed circuit board 124 corresponding to jack 122-1 similarly includes a plurality of metal-plated apertures 171'-178' that receive the termination ends of the contact wires of jack 122-1, and a plurality of metal-plated apertures 191'-198' that each receive a termination of an IDC of jack 122-1. A plurality of conductive paths (unnumbered in FIG. 9) are provided that connect each of the metal-plated apertures 171'-178' to a respective one of the metal-plated apertures 191'-198'.

As shown in FIG. 9, the printed circuit board 124 may include a plurality of plate capacitors (e.g., plate capacitors 125, 126) and/or spirals (spirals 127, 128) that may be used to provide single or multi-stage crosstalk compensation for "internal" near-end and/or far-end crosstalk that is generated between the four differential pairs of conductive paths through jack 122-2. In the particular embodiment shown in FIG. 9, multi-stage internal crosstalk compensation is provided between differential pairs 1 and 3, differential pairs 2 and 3, and differential pairs 3 and 4 of jack 122-2, and single stage internal crosstalk compensation is provided between differential pairs 1 and 2 and differential pairs 1 and 4 of jack 122-2. As the use of single and multi-stage crosstalk compensation circuits for cancellation of internal crosstalk in a communications jack is well-known in the art, further explanation of these crosstalk circuits will not be provided herein.

As can also be seen in FIG. 9, the printed circuit board 124 may further include a plurality of near-end alien crosstalk compensation circuits 210, 220, 230, 240 that compensate for near-end alien crosstalk generated between the IDCs of jack 122-2 and the two jacks 122-1 and 122-3 adjacent thereto. In this particular embodiment, each of circuits 210, 220, 230, 240 are two-stage near-end alien crosstalk compensation circuits. Near-end alien crosstalk compensation circuit 210 provides near-end alien crosstalk compensation between pair 2 of jack 122-2 and pair 1 of jack 122-1. Near-end alien crosstalk compensation circuit 220 provides near-end alien crosstalk compensation between pair 3 of jack 122-2 and pair 4 of jack 122-1. Near-end alien crosstalk compensation circuit 230 provides near-end alien crosstalk compensation between pair 4 of jack 122-2 and pair 3 of jack 122-3. Finally, near-end alien crosstalk compensation circuit 240 provides near-end alien crosstalk compensation between pair 1 of jack 122-2 and pair 2 of jack 122-3.

Near-end alien crosstalk compensation circuit 210 includes a first stage 211 and a second stage 212. The first stage 211 comprises a first capacitor 213 that is coupled between metal-plated IDC aperture 191 of jack 122-2 and a metal-plated IDC aperture 195' of jack 122-1, and a second capacitor 215 that is coupled between metal-plated IDC aperture 192 of jack 122-2 and a metal-plated IDC aperture 194' of jack 122-1. A conductive trace 214a connects the metal-plated aperture 191 that receives IDC 181 to the first electrode of the first capacitor 213 and a conductive trace 214b connects the metal-plated aperture 195' of jack 122-1 to the second electrode of the first capacitor 213. As trace 214a is not part of the signal current carrying path through the jack 122-2 from IDC 181 to jackwire contact 160-1, the first capacitor 213 may be at a very small delay from the IDC 181. As discussed above, the near-end alien crosstalk may arise mostly in the IDCs, and hence the first capacitor 213 may inject compensatory crosstalk very close in time to the time when the offending alien crosstalk is generated.

A conductive trace 216a connects the metal-plated aperture 192 that receives IDC 182 to the first electrode of capacitor 215, and a conductive trace 216b connects the metal-plated aperture 194' of jack 122-1 to the second electrode of second capacitor 215. Trace 216a is not part of the signal current carrying path through the jack 122-2 from IDC 192 to jackwire contact 160-2, and hence the second capacitor 215 may also be at a very small delay from the IDC 182 such that it injects compensatory crosstalk very close to the region where the offending alien crosstalk arises. The first and second capacitors 213, 215 may be designed so that together they generate a compensatory crosstalk vector having a magnitude that exceeds the magnitude of the near-end alien crosstalk generated between the IDCs 181, 182 of jack 122-2 and the IDCs in the metal-plated IDC apertures 194', 195' of jack 122-1, and that has a polarity that is generally opposite the polarity of the near-end alien crosstalk generated between the IDCs 181, 182 of jack 122-2 and the IDCs in the metal-plated IDC apertures 194', 195' of jack 122-1.

The second stage 212 of near-end alien crosstalk compensation circuit 210 comprises a third capacitor 217 that is coupled between the metal-plated aperture 172 that receives jackwire contact 160-2 of jack 122-2 and the metal-plated aperture 175' of jack 122-1. A conductive trace 218a connects the metal-plated aperture 172 to the first electrode of the third capacitor 217 and a conductive trace 218b connects the metal-plated aperture 175' to the second electrode of the third capacitor 217. As explained in the aforementioned '358 patent, the magnitude and phase of the crosstalk vector generated by the third capacitor 217 may be selected so that the crosstalk generated by the combination of the first stage 211 and the second stage 212 substantially cancels the near-end alien crosstalk that arises between pair 2 of jack 122-2 and pair 1 of jack 122-1, at least at one frequency (or over a frequency range of interest). It will also be appreciated that while second stage 212 is implemented as a single capacitor 217 in the depicted embodiment, in other embodiments it may be implemented in a variety of different ways (e.g., multiple capacitors, inductors and capacitors, inductors only, etc.).

Near-end alien crosstalk compensation circuit 220 includes a first stage 221 and a second stage 222. The first stage 221 comprises a first capacitor 223 that is coupled between metal-plated IDC aperture 193 of jack 122-2 and a metal-plated IDC aperture 197' of jack 122-1, and a second capacitor 225 that is coupled between metal-plated IDC aperture 196 of jack 122-2 and a metal-plated IDC aperture 198' of jack 122-1. The capacitors 223, 225 are connected to the above-identified metal-plated IDC apertures via respective conductive traces that are not part of any signal current carrying path, and thus the capacitors 223, 225 may each be at a very small delay from the respective IDCs that they are connected to. The first and second capacitors 223, 225 may be designed so that together they generate a compensatory crosstalk vector having a magnitude that exceeds the magnitude of the near-end alien crosstalk generated between the IDCs 183, 186 of jack 122-2 and the IDCs in the metal-plated IDC apertures 197', 198' of jack 122-1, and that has a polarity that is generally opposite the polarity of the near-end alien crosstalk generated between the IDCs 183, 186 of jack 122-2 and the IDCs in the metal-plated IDC apertures 197', 198' of jack 122-1.

The second stage 222 of near-end alien crosstalk compensation circuit 220 comprises a third capacitor 227 that is coupled between the metal-plated aperture 176 that receives jackwire contact 160-6 of jack 122-2 and the metal-plated aperture 177' of jack 122-1. The magnitude and phase of the crosstalk vector generated by the third capacitor 227 may be selected so that the crosstalk generated by the combination of the first stage 221 and the second stage 222 substantially cancels the near-end alien crosstalk that arises between pair 3 of jack 122-2 and pair 4 of jack 122-1, at least at one frequency (or over a frequency range of interest).

Near-end alien crosstalk compensation circuit 230 provides compensation between pair 4 of jack 122-2 and pair 3 of jack 122-3, and includes a first stage 231 and a second stage 232. As jack 122-3 is not visible in FIG. 9, only a portion of the near-end alien crosstalk compensation circuit 230 is shown. Near-end alien crosstalk compensation circuit 230 may be identical to near-end alien crosstalk compensation circuit 220, except that it provides pair 4/pair 3 compensation between jacks 122-2 and 122-3 instead of between jacks 122-1 and 122-2 like circuit 220. Accordingly, further description of near-end alien crosstalk compensation circuit 230 will be omitted.

Near-end alien crosstalk compensation circuit 240 provides compensation between pair 1 of jack 122-2 and pair 2 of jack 122-3, and includes a first stage 241 and a second stage 242. As jack 122-3 is not visible in FIG. 9, only a portion of the near-end alien crosstalk compensation circuit 240 is shown. Near-end alien crosstalk compensation circuit 240 may be identical to near-end alien crosstalk compensation circuit 210, except that it provides pair 2/pair 1 compensation between jacks 122-2 and 122-3 instead of between jacks 122-1 and 122-2 like Circuit 210. Accordingly, further description of near-end alien crosstalk compensation circuit 240 will be omitted.

In addition, printed circuit board 124 further includes a single stage near-end alien crosstalk compensation circuit 250. Near-end alien crosstalk compensation circuit 250 compensates for near-end alien crosstalk that arises between the contact wires and/or circuit traces of pair 4 of jack 122-1 and the contact wires and/or circuit traces of pair 1 of jack 122-2. As shown in FIG. 9, the crosstalk compensation circuit 250 comprises a capacitor 253 that is coupled between metal-plated aperture 177' of jack 122-1 and a metal-plated aperture 174 of jack 122-2 via respective conductive traces that are not part of any signal current carrying path. The capacitor 253 may be designed to generate a compensatory crosstalk vector having a magnitude that is equal to the magnitude of the near-end alien crosstalk generated between the contact wires and/or circuit traces of pair 4 of jack 122-1 and the contact wires and/or circuit traces of pair 1 of jack 122-2, and that has a polarity that is generally opposite the polarity of the near-end alien crosstalk generated between the contact wires and/or circuit traces of pair 4 of jack 122-1 and the contact wires and/or circuit traces of pair 1 of jack 122-2.

While the embodiment of FIG. 9 only includes a single near-end alien crosstalk compensation circuit 250 that is designed to compensate for near-end alien crosstalk that arises between the contact wires and/or circuit traces of adjacent jacks, it will be appreciated that additional such circuits may be provided in further embodiments. It will also be appreciated that, in some embodiments, the near-end alien crosstalk compensation circuit 250 may be implemented as a multi-stage crosstalk compensation circuit, as may any additional near-end alien crosstalk compensation circuits that are provided for compensating additional near-end alien crosstalk that arises between the contact wires and/or circuit traces of adjacent jacks.

Figure 10:
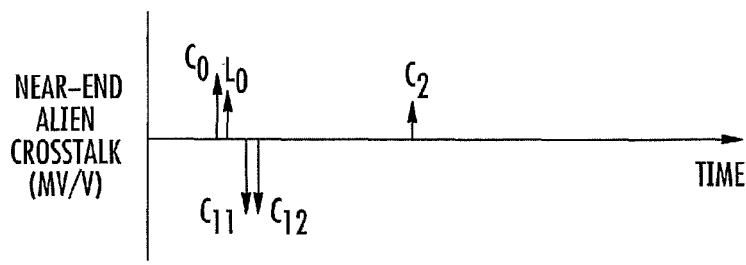
FIG. 10 is a schematic graph that illustrates the offending and compensating near-end alien crosstalk in a jack that may be used in embodiments of the present invention.

FIG. 10 is a timeline illustrating the alien crosstalk that arises on the conductors of pair 2 of jack 122-2 when a signal is transmitted over pair 1 of jack 122-1.

Referring to FIGS. 7 and 9, it can be seen that the IDC that is received within the metal-plated aperture 194' of jack 122-1 couples with both IDC 181 and IDC 182 of jack 122-2. As current runs through the IDC that is received within the metal-plated aperture 194' of jack 122-1, this coupling will comprise both inductive coupling and capacitive coupling (which results from the facing planar surfaces of the IDCs. In communications insert 120, IDC 184' of jack 122-1 couples more strongly with IDC 181 of jack 122-2 than it does with IDC 182 of jack 122-2. As a result of this unequal coupling, offending near-end alien crosstalk arises between pair 2 of jack 122-2 and pair 1 of jack 122-1. The inductive component of this offending near-end alien crosstalk is represented by vector $L_0$ in FIG. 10, and the capacitive component of this offending near-end alien crosstalk is represented by vector $C_0$ in FIG. 10. The vectors $C_0$ and $L_0$ may be almost co-located on the time axis. As shown in FIG. 10, the capacitive component $C_0$ tends to be larger than the inductive component $L_0$ as the facing IDCs effectively form a plate capacitor.

The first and second capacitors 213, 215 of the first stage 211 of the near-end alien crosstalk compensation circuit 210 each generates a compensatory crosstalk vector. These are illustrated in FIG. 10 as vectors $C_{11}$ and $C_{12}$. As the first stage 211 is implemented using capacitors only, the first stage compensation is solely capacitive compensation. As shown in FIG. 10, the combined magnitudes of $C_{11}$ and $C_{12}$ exceeds the combined magnitudes of $L_0$ and $C_0$. As capacitors 213 and 215 are located at nearly zero delay from IDCs 181 and 182, respectively, the compensating crosstalk vectors $C_{11}$ and $C_{12}$ that they generate may be almost co-located on the time axis of FIG. 10.

The third capacitor 217 that forms the second stage 212 of the near-end alien crosstalk compensation circuit 210 generates a compensatory crosstalk vector $C_2$ that has the same polarity of the offending crosstalk vectors $C_0$ and $L_0$ and provides solely capacitive compensation. The first and second stages 211, 212 may be designed so that the vector sum of the vectors $C_0$, $L_0$, $C_{11}$, $C_{12}$ and $C_2$ of FIG. 10 may be maintained below specified levels over a frequency range of interest, as will be discussed further below with respect to FIGS. 11-12.

Figure 11:
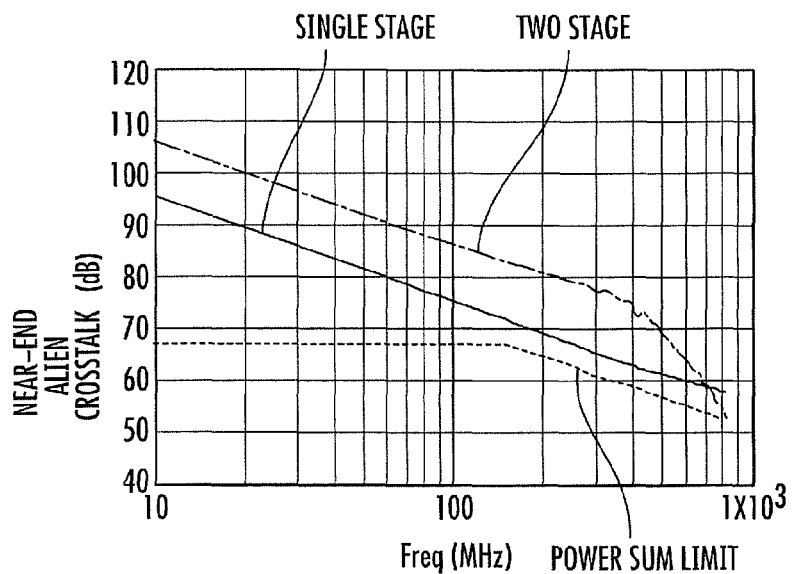
FIG. 11 is a graph illustrating the simulated near-end alien crosstalk performance for two adjacent jacks in a patch panel when both single-stage and multi-stage near-end alien crosstalk compensation is used.

FIG. 11 is a graph illustrating the simulated near-end alien crosstalk between pair 2 on jack 122-2 and pair 1 on jack 122-1 for (1) a modified version of the patch panel 100 of FIG. 5 in which single-stage near-end alien crosstalk compensation is provided between these pairs (labeled "Single Stage" in FIG. 11) and (2) the patch panel 100 of FIG. 5 which provides multi-stage near-end alien crosstalk compensation for this pair combination via crosstalk compensation circuit 210 (labeled "Two-Stage" in FIG. 11). In the modified version of the patch panel 100 that was used to generate the "Single Stage" curve in FIG. 11, the second stage 212 of crosstalk compensation circuit 210 was removed, and the magnitude of the capacitors 213, 215 in the first stage 211 of crosstalk compensation circuit 210 were adjusted to match the magnitudes of the offending near-end alien crosstalk from pair 1 of jack 122-1. The graph of FIG. 11 also includes a "Power Sum Limit" line, which is the limit under the TIA/EIA Category 6A standard for the power sum of the alien crosstalk on all four differential pairs of jack 122-2 that results when a signal is transmitted over, for example, pair 1 of jack 122-2.

As shown by the "Single-Stage" curve in FIG. 11, using single-stage near-end alien crosstalk compensation, the near-end alien crosstalk for the pair 2/pair 1 combination is only about 5 dB below the power sum limit at frequencies above about 150 MHz. When the contribution of the other three differential pairs is added in, the near-end alien crosstalk is within a few dB of the power sum limit, indicating that there is little near-end alien crosstalk margin. In contrast, the "Two-Stage" curve in FIG. 11 shows that when multi-stage alien crosstalk compensation is employed, the near-end alien crosstalk for the pair 2/pair 1 combination is at least 13 dB below the power sum limit at all frequencies below 500 MHz. It is also apparent from FIG. 11 that the use of multi-stage compensation provides an improvement in near-end alien crosstalk performance of between about 8 dB and about 12 dB for all frequencies in the 150 MHz to 500 MHz frequency range.

Figure 12:
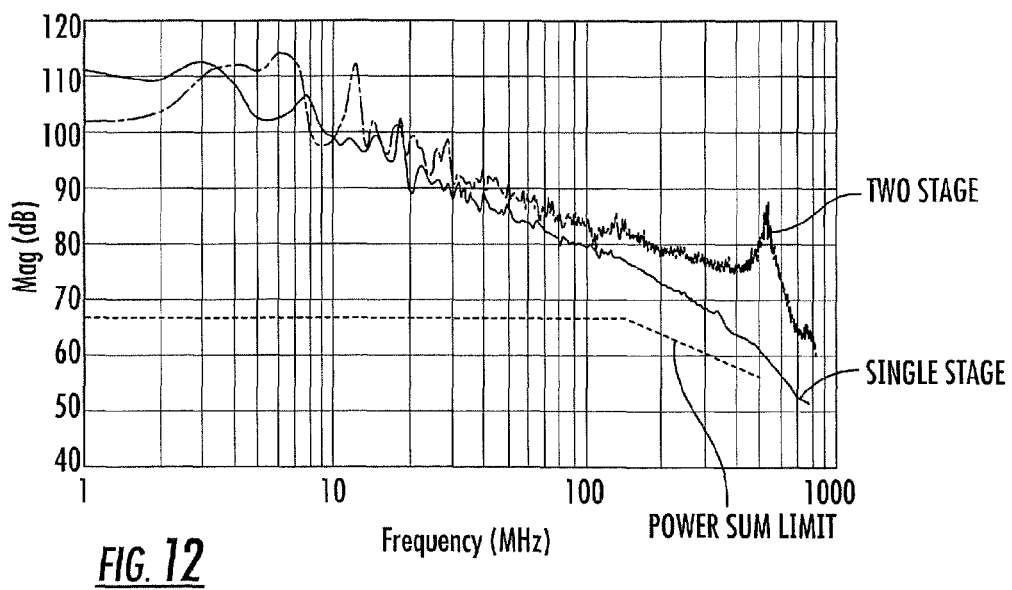
FIG. 12 is a graph illustrating the measured near-end alien crosstalk performance for two adjacent jacks in a patch panel when both single-stage and multi-stage near-end alien crosstalk compensation is used.

FIG. 12 is a graph illustrating the measured near-end alien crosstalk between pair 2 on jack 122-2 and pair 1 on jack 122-1 for (1) the modified version of the patch panel 100 of FIG. 5 in which single-stage near-end alien crosstalk compensation is provided between these pairs ("Single-Stage" curve) and (2) the patch panel 100 of FIG. 5 ("Two-Stage" curve). As shown in FIG. 12, the measured performance closely tracked the simulated performance of FIG. 11.

As discussed above, according to some embodiments of the present invention, the multi-stage near-end alien crosstalk compensation circuits may provide only capacitive alien crosstalk compensation. As known to those of skill in the art, in conventional modular communication plug-jack connections, capacitively coupled and inductively coupled signal components add for NEXT, while they subtract for FEXT. That is:

$$NEXT = X_C + X_M$$

and $$FEXT = X_C - X_M$$

where $X_C$ is the capacitively coupled component, and $X_M$ is the inductively coupled component. Thus, if the offending crosstalk includes both a capacitively coupled component and an inductively coupled component, which is generally the case in conventional modular plug-jack connections, then a crosstalk compensation circuit will need both capacitive and inductive components to cancel out both the offending NEXT and FEXT.

Pursuant to embodiments of the present invention, it has been discovered that for alien crosstalk compensation, all capacitive crosstalk compensation circuits can be used, where the amount of Capacitive compensation may be selected to approximately cancel the near-end alien crosstalk over a desired frequency range. As shown by the above equations, use of such an all capacitive crosstalk compensation circuit generally will not approximately cancel the offending far-end alien crosstalk. However, this far-end alien crosstalk may be addressed in other ways such as, for example, reducing the amount of inductive coupling between differential pairs within adjacent connectors.

As shown in FIG. 9, in some embodiments, the alien crosstalk compensation circuit may be implemented using printed circuit board capacitors. The capacitors may be, for example, plate capacitors, inter-digitated finger capacitors, or two dead-end traces that run immediately adjacent to each other, either by running immediately adjacent to each other on the same layer of the printed circuit board, or by running immediately adjacent to each other on adjacent layers of the printed circuit board. In many embodiments, the capacitors may be implemented as adjacent such dead end traces as typically only a small amount of capacitive compensation is required due to the generally low levels of near-end alien crosstalk that is generated between the IDCs (or other output terminals) of adjacent jacks.

It will also be appreciated that in conventional patch panel designs, the primary source of alien crosstalk may be coupling between the output terminals (e.g., IDCs) of adjacent jacks in the panel. Such coupling results because of the very close spacing of the jacks in the panel, which necessarily means that the output terminals of adjacent jacks may be in close proximity to each other. Moreover, to minimize internal crosstalk, the output terminals are often spaced at the periphery of the jacks, bringing the output terminals of adjacent jacks into close proximity. In a conventional IDC, an insulated copper wire from a cable is inserted into a sharp-edged slot in the IDC that slits the insulation and the IDC thereby makes mechanical and electrical contact with the copper wire. This slot usually extends about halfway down the IDC. Electrical signals thus couple onto the IDC about halfway down the IDC, and must then travel the rest of the way down the IDC to the base of the IDC to couple onto the printed circuit board that receives the IDC.

As the coupling between adjacent jacks is primarily in the IDCs, the alien crosstalk will typically have an inductive component due to the current travelling from the copper wires to the printed circuit board down the lower half of the facing IDCs. As a result, there typically is some amount of delay between the location where the offending crosstalk arises and the location of the first stage of any multi-stage alien crosstalk compensation circuit. In order to minimize this delay, the first stage alien crosstalk compensation may be implemented as one or more capacitors that are connected directly to the base of the IDCs or the metal-plated apertures that receive the bases of the IDCs by dead-end circuit traces. Since capacitors that are located on branches off of the signal current carrying path generally appear on the timeline of FIG. 10 at just after the point where the dead-end branch connects to the signal current carrying path, connecting the capacitors to the base of the IDCs may serve to minimize the delay between the offending crosstalk and the first stage crosstalk compensation. By minimizing this delay, it is generally possible to achieve improved crosstalk compensation.

As discussed above with respect to the discussion of FIG. 9, according to some embodiments of the present invention, a first near-end alien crosstalk compensation circuit may be provided that compensates for near-end alien crosstalk that arises in the IDCs of a first pair of a first jack (e.g., circuit 240 which provides such compensation for pair 1 of jack 122-2 with respect to pair 2 of jack 122-3), and a second near-end alien crosstalk compensation circuit may be provided that compensates for near-end alien crosstalk that arises in the contact wires and/or circuit traces of the first pair of the first jack (e.g., circuit 250 which provides such compensation for pair 1 of jack 122-2 with respect to pair 4 of jack 122-1). Each such circuit may have a compensation stage that is located at a very small delay from the source of the near-end alien crosstalk that the circuit is designed to compensate for.

While embodiments of the present invention have primarily been discussed herein with respect to jacks that include eight conductive paths that are arranged as four differential pairs of conductive paths, it will be appreciated that the concepts described herein are equally applicable to connectors that include other numbers of differential pairs. It will also be appreciated that the techniques according to embodiments of the present invention may be employed on jacks that have output terminals other than IDCs. Additionally, in some embodiments, the multi-stage near-end alien crosstalk compensation circuit may include inductive crosstalk compensation components. It will further be appreciated that the number of multi-stage near-end alien crosstalk compensation circuits provided between a particular jack and the jacks adjacent to it may be varied from the number shown in the exemplary embodiments depicted herein.

It will also be appreciated that jacks, patch panels and other devices according to embodiments of the present invention may include both multi-stage near-end alien crosstalk compensation circuits that compensate for alien crosstalk in the output terminals as well as additional circuits that compensate for alien crosstalk that arises in other portions of the jack. For example, alien crosstalk may also arise in the input terminals (e.g., jackwire contacts) of a jack. In the patch panel described above with respect to FIGS. 5-9, the jackwires for contact wire positions 3 and 6 in the TIA 568 type B contact wire numbering scheme (i.e., jackwire contacts 160-3 and 160-6) cross over each other. As explained, for example, in co-pending U.S. patent application Ser. No. 12/264,498, filed Nov. 4, 2008, this cross-over may reduce mode conversion in the jackwire contacts that may give rise to alien crosstalk.

Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

What is claimed is:

1. A communications connector system, comprising:
a first communications connector that includes a first output terminal and a second output terminal, the first and second output terminals being connected to respective first and second conductive paths through the first communications connector, the first and second conductive paths forming a first differential pair of conductive paths through the first communications connector;
a second communications connector that includes a third output terminal and a fourth output terminal, the third and fourth output terminals being connected to respective third and fourth conductive paths through the second communications connector, the third and fourth conductive paths forming a second differential pair of conductive paths through the second communications connector, the second communications connector being immediately adjacent to the first communications connector and arranged such that a first signal coupling level from the first output terminal to the third output terminal in response to a first communication signal that is transmitted through the first differential pair of conductive paths exceeds a second signal coupling level from the first output terminal to the fourth output terminal in response to the first communication signal; and
a multi-stage near-end alien crosstalk compensation circuit having at least a first stage and a second stage that is configured to compensate for near-end alien crosstalk between the first and second differential pairs of conductive paths,
wherein the polarity of the near-end alien crosstalk introduced in the first stage is generally opposite the polarity of the near-end alien crosstalk introduced in the second stage and is also generally opposite the polarity of the near-end alien crosstalk introduced in the first through fourth output terminals.

2. The communications connector system of claim 1, wherein the first, second, third and fourth output terminals are mounted on a common printed circuit board.

3. The communications connector system of claim 1, wherein the multi-stage near-end alien crosstalk compensation circuit consists, only of capacitive compensation elements.

4. The communications connector system of claim 1, wherein the multi-stage near-end alien crosstalk compensation circuit increases the far-end alien crosstalk between the first and second differential pairs of conductive paths.

5. The communications connector system of claim 1, wherein the first stage of the multi-stage near-end alien crosstalk compensation circuit is located at substantially no delay from a base of the first output terminal.

6. The communications connector system of claim 2, wherein the first stage of the multi-stage near-end alien crosstalk compensation circuit comprises a first capacitor between the first conductive path and the fourth conductive path and a third capacitor between the second conductive path and the third conductive path.

7. The communications connector system of claim 6, wherein the first capacitor is located at substantially no delay from a base of the first output terminal that is received in the common printed circuit board.

8. The communications connector system of claim 6, wherein the first capacitor comprises a section of a first conductive trace that is a dead-end branch off of the first conductive path that runs immediately adjacent to a section of a second conductive trace that is a dead-end branch off of the fourth conductive path.

9. The communications connector system of claim 1, further comprising a third communications connector that is adjacent to the second communications connector such that the second communications connector is between the first and third communications connectors, wherein the third and fourth output terminals comprise a first differential pair of output terminals on the second communications connector and the first and second output terminals comprise a first differential pair of output terminals on the first communications connector, wherein the second communications connector further comprises:

a second multi-stage near-end alien crosstalk compensation circuit that is configured to compensate for alien crosstalk between a second differential pair of output terminals on the second communications connector and a second differential pair of output terminals on the first communications connector;

a third multi-stage near-end alien crosstalk compensation circuit that is configured to compensate for alien crosstalk between a third differential pair of output terminals on the second communications connector and a first differential pair of output terminals on the third communications connector; and a fourth multi-stage near-end alien crosstalk compensation circuit that is configured to compensate for alien crosstalk between a fourth differential pair of output terminals on the second communications connector and a second differential pair of output terminals on on the third communications connector.

10. The communications connector system of claim 1, wherein the first communications connector further includes a fifth output terminal and a sixth output terminal, the fifth and sixth output terminals being connected to respective fifth and sixth conductive paths through the first communications connector, the fifth and sixth conductive paths forming a third differential pair of conductive paths through the first communications connector, and wherein the communications connector system further comprises a near-end alien crosstalk compensation circuit having at least a first stage that is configured to compensate for near-end alien crosstalk between the second and third differential pairs of conductive paths.

11. The communications connector system of claim 1, wherein the communications connector system comprises a patch panel that includes a mounting frame, and wherein the first communications connector and the second communications connector are mounted immediately adjacent to each other on the mounting frame.

12. The communications connector system of claim 1, wherein the first, second, third and fourth output terminals comprise insulation displacement contacts ("IDCs").

13. The communications connector system of claim 2, wherein the first stage of the multi-stage near-end alien crosstalk compensation circuit comprises a first capacitor between the first conductive path and the fourth conductive path and wherein the second stage of the multi-stage near-end alien crosstalk compensation circuit comprises a second capacitor between at least one of the first conductive path and the third conductive path or between the second conductive path and the fourth conductive path.

14. The communications connector system of claim 13, wherein a first delay corresponding to a time it takes the first communication signal to travel from the output terminals that are connected to the first differential pair of conductive paths to the first capacitor is less than a second delay that corresponds to a time that it takes the first communication signal to travel from the output terminals that are connected to the first differential pair of conductive paths to the second capacitor.

15. The communications connector system of claim 13, wherein a first electrode of the first capacitor is directly connected to a first metal-plated aperture in the common printed circuit board that receives the first output terminal via a dead-end branch off of the first conductive path, and wherein the second electrode of the first capacitor is directly connected to a second metal-plated aperture in the common printed circuit board that receives the fourth output terminal via a dead-end branch off of the fourth conductive path.

16. The communications connector system of claim 13, further comprising a third capacitor between the second conductive path and the third conductive path that is part of the first stage of the multi-stage near-end alien crosstalk compensation circuit.

* * * * *

UNITED STATES PATENT AND TRADEMARK OFFICE
CERTIFICATE OF CORRECTION

| | | |
|---|---|---|
| PATENT NO. | : 7,976,349 B2 | Page 1 of 1 |
| APPLICATION NO. | : 12/632855 | |
| DATED | : July 12, 2011 | |
| INVENTOR(S) | : Heckmann | |

It is certified that error appears in the above-identified patent and that said Letters Patent is hereby corrected as shown below:

In the Claims:
Column 22, Claim 3, Line 35: Please correct "consists, only" to read -- consists only --

Signed and Sealed this
Eighteenth Day of October, 2011

David J. Kappos
*Director of the United States Patent and Trademark Office*